(12) United States Patent
Takeo et al.

(10) Patent No.: US 7,027,631 B2
(45) Date of Patent: Apr. 11, 2006

(54) METHOD AND SYSTEM FOR DETECTING SUSPECTED ANOMALOUS SHADOWS

(75) Inventors: Hideya Takeo, Kaisei-machi (JP);
Takashi Imamura, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 662 days.

(21) Appl. No.: 09/941,748

(22) Filed: Aug. 30, 2001

(65) Prior Publication Data

US 2002/0041702 A1    Apr. 11, 2002

(30) Foreign Application Priority Data

Aug. 31, 2000  (JP) ............................. 2000-263640
Jul. 13, 2001  (JP) ............................. 2001-213865

(51) Int. Cl.
*G06K 9/00*    (2006.01)

(52) U.S. Cl. ...................... 382/132; 382/128; 378/207

(58) Field of Classification Search ................ 382/128, 382/132; 378/207; 324/300
See application file for complete search history.

(56) References Cited

U.S. PATENT DOCUMENTS

| | | | | |
|---|---|---|---|---|
| 5,095,499 A | * | 3/1992 | Wentz .......................... | 378/37 |
| 5,133,020 A | * | 7/1992 | Giger et al. ................ | 382/128 |
| 5,544,238 A | * | 8/1996 | Galkin ........................ | 378/207 |
| 5,583,346 A | * | 12/1996 | Nakajima .................... | 250/587 |
| 5,761,334 A | * | 6/1998 | Nakajima et al. ........... | 382/132 |
| 6,370,480 B1 | * | 4/2002 | Gupta et al. ................. | 702/39 |
| 6,415,053 B1 | * | 7/2002 | Norimatsu .................. | 382/199 |
| 6,694,047 B1 | * | 2/2004 | Farrokhnia et al. ......... | 382/132 |
| 2001/0019623 A1 | * | 9/2001 | Takeo ......................... | 382/128 |

FOREIGN PATENT DOCUMENTS

| | | |
|---|---|---|
| JP | 8-287230 | 11/1996 |
| JP | 8-294479 | 11/1996 |

OTHER PUBLICATIONS

Electronic Information Communication Society Journal, D-II, vol. J75-D-II, No. 7, p. 1170, 1992.
Medical Imaging Technology, vol. 12, No. 1, 1994.
Proceeding of Electronic Information and Communication Conference, D-II, vol. J75-D-II, No. 3.

* cited by examiner

*Primary Examiner*—Jingge Wu
*Assistant Examiner*—Craig Kronenthal
(74) *Attorney, Agent, or Firm*—Sughrue Mion, PLLC (57) ABSTRACT

An anomalous shadow detection system capable of obtaining stable detection capacity across all facilities into which the system is introduced, regardless of variations in the conditions of the image obtaining environments of each facility is provided. An image obtaining means obtains an image of a standard-phantom, and an image readout means obtains phantom-image data thereof. Said phantom-image data is input to an evaluative model detecting means which detects evaluative models contained within the image of the standard-phantom. An evaluating means compares the detected evaluative models to a desired detection level. If the detected evaluative models are of a different detection level than the desired detection level, a parameter setting means resets the detection parameter, depending on the result obtained by the evaluating means 32, and the above processing of the phantom-image data is repeated until the detection result and the desired detection level are the same.

18 Claims, 8 Drawing Sheets

| $f_7$ | $f_6$ | $f_5$ | $f_4$ | $f_3$ |
|---|---|---|---|---|
| $f_8$ | | | | $f_2$ |
| $f_9$ | | PIXEL j | | $f_1$ |
| $f_{10}$ | | | | $f_{16}$ |
| $f_{11}$ | $f_{12}$ | $f_{13}$ | $f_{14}$ | $f_{15}$ |

METHOD AND SYSTEM FOR DETECTING SUSPECTED ANOMALOUS SHADOWS

BACKGROUND OF THE INVENTION

1. Field of the Invention

The present invention relates generally to a method and system for detecting suspected anomalous shadows, and more particularly to a method and system for setting a threshold value matched to the image obtaining environment, and detecting suspected anomalous shadows.

2. Description of the Related Art

In the field of medical radiology//suspected anomalous shadow detection systems, the diagnostic reading of radiation images in order to discover the location of a disease, or to observe the state of a diseased tissue in order to determine the presence or absence of disease or the course of a disease, is widely practiced. However, the results and reliability of such diagnosis depends largely on the experience and skill level of the examiner, and is by no means a purely objective measure.

Take for example a case in which a mammogram (a diagnostic radiation image of the mammary glands) is obtained for the purpose of diagnosing whether or not breast cancer is present. It is necessary to detect the anomalous shadows contained therein that have been cast by tumors and microcalcifications, which are indicative of breast cancer. However, it is not a forgone conclusion that an examiner will be able to correctly specify the exact range defining such anomalous shadows. Therefore, an objective and reliable method and system for detecting anomalous shadows, starting with the shadows of tumors and microcalcifications, which is not dependent on the skill level of the examiner, is called for.

In response to this need, based on the image data of a target subject that has been obtained as a diagnostic image, anomalous shadow detection systems have been proposed that automatically detect anomalous shadows suspected of having been cast by tumors or microcalcifications indicative of breast cancer (hereinafter referred to as suspected anomalous shadows) from the image represented by said image data, by use of a computer (computer assisted image diagnostic apparatus and CAD systems) (see, e.g., Japanese Unexamined Patent Publication Nos. 8(1996)-294479, 8(1996)-287230, etc.).

Such anomalous shadow detection systems detect suspected anomalous shadows based on the pixel values (i.e., image data) that can be considered representative thereof, and display a mark in the areas in which the suspected anomalous shadows occur, so as to alert an examiner of the subject image to positions thereof; alternatively, by quantitatively posting (as numerical data) the characteristic features of the detected suspected anomalous shadows, objectivity in the diagnosis of the subject radiation image is bolstered, and the oversight or misconstrual of the detected suspected anomalous shadows such as those described above is thereby prevented. According to the above-described processing employed in detecting suspected anomalous shadows, an iris filtering process appropriate for detecting mainly suspected anomalous shadows of tumors, a morphology filtering process appropriate for detecting mainly suspected anomalous shadows of microcalcifications, and etc. are utilized.

The expression "iris filtering process" refers to an effective means of detecting regions within an image suspected of containing anomalous shadows of tumors, which are one characteristic feature of breast cancer in mammary glands appearing in a mammogram, by comparing the output value of the iris filter, which represents the largest value of the concentration of the density slopes of the image signal to a predetermined threshold value.

Taking for example a radiation image recorded on an X-ray film (an image represented by a high-density, high signal-level image signal), it is known that the image density of the shadow of a tumor is slightly lower than that of the peripheral region thereof; and a pattern has been recognized wherein the image density slope of the internal area the shadow of a tumor is denser for points toward the substantially circular perimeter and becomes less dense toward the center. Therefore, each point within the shadow of a tumor has a local image density slope pointing to the center of the shadow.

The term "iris filtering" refers to computing as a slope vector the slope of the image-signal, which is represented by the density value, and outputting the concentration of said slope vector; the iris filtering process is the detecting, based on the concentration of the slope vectors, of the suspected regions of the anomalous shadows of tumors.

Hereinafter, referring to the mammogram shown in FIG. 1, an explanation of the iris filtering process will be given. The slope vectors of the pixels within the internal section of a shadow P1 of a tumor occurring in an original image data P, as shown in (2) of FIG. 1, point substantially to the center of the shadow P1 of the tumor, whereas the slope vectors of an elongated anomalous shadows P2, such as that of a blood vessel, a mammary gland, etc., as shown in (3) of FIG. 1, do not point to any particular point. Therefore, if, by evaluating the local distribution of the directions of the slope vectors, a spot is detected toward which the slope vectors therein point (or are concentrated at), said spot can be selected as a suspected region of an anomalous shadow of a tumor. Further, a shadow P3 of the point at which two elongated shadows of mammary glands, etc. cross, as shown in (4) of FIG. 1, is detected as a pseudo-suspected region because there is a tendency for the slope vectors thereof to point to a particular point.

Hereinafter, an algorithm for the iris filtering process will be shown.

First, the direction θ representing the orientation of the slope vector of the image data is computed for each pixel j forming the subject image using the equation (1) below.

$$\theta = \tan^{-1} \frac{(f_3 + f_4 + f_5 + f_6 + f_7) - (f_{11} + f_{12} + f_{13} + f_{14} + f_{15})}{(f_1 + f_2 + f_3 + f_{15} + f_{16}) - (f_7 + f_8 + f_9 + f_{10} + f_{11})} \quad (1)$$

Figure 1A:
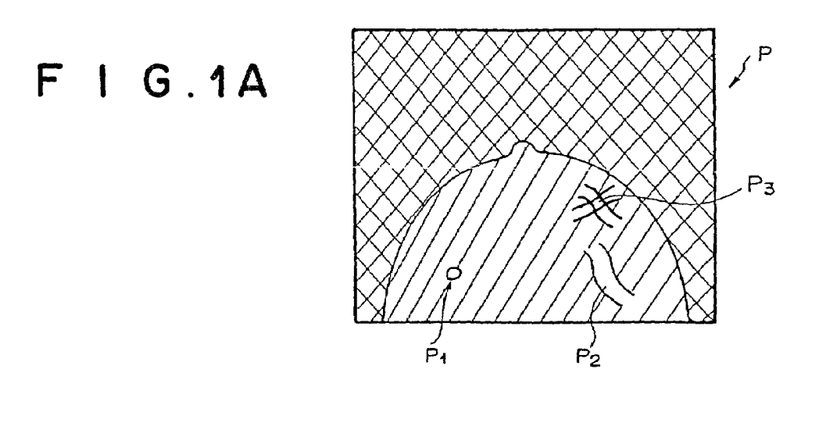
FIGS. 1A, 1B, 1C, and 1D illustrate the operation of the iris filtering process.
Figure 1B:
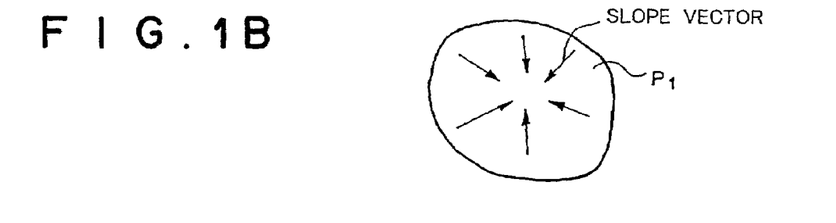
Figure 1C:
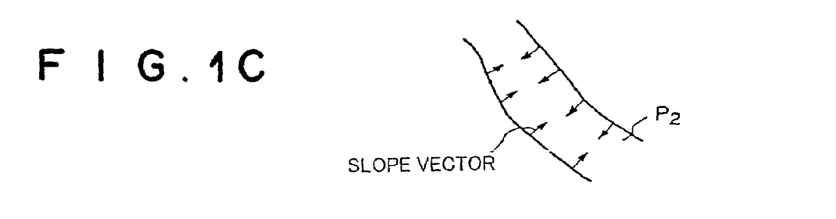
Figure 1D:
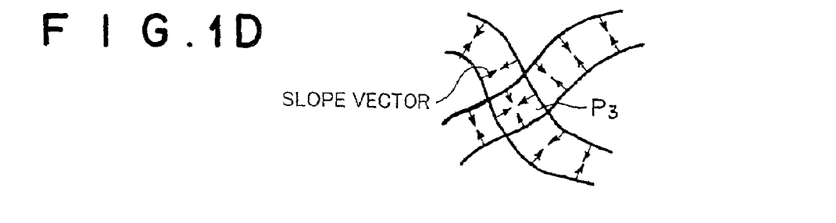
Figure 2:
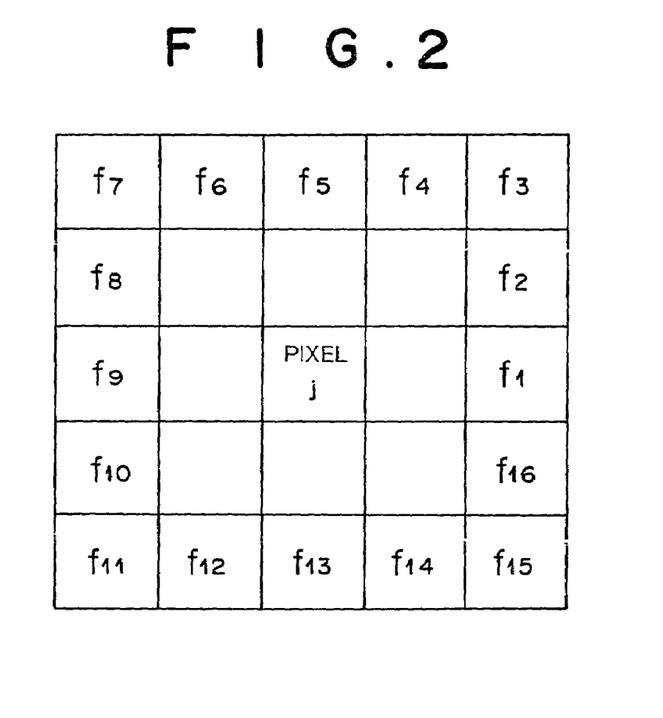
FIG. 2 shows a 5×5 pixel mask centered on a pixel j.

Here, each of f1–f16, as shown in FIG. 2, represent a pixel value (i.e., image data) corresponding to one of the outermost pixels of a mask of a 5×5 pixels centered on the pixel j.

Next, the concentration C of the slope vectors toward the pixel of interest is computed for each pixel forming the subject image, taking that pixel as the pixel of interest, by using the following equation (2).

$$C = (1/N) \sum_{j=1}^{N} \cos\theta_j \quad (2)$$

Figure 3:
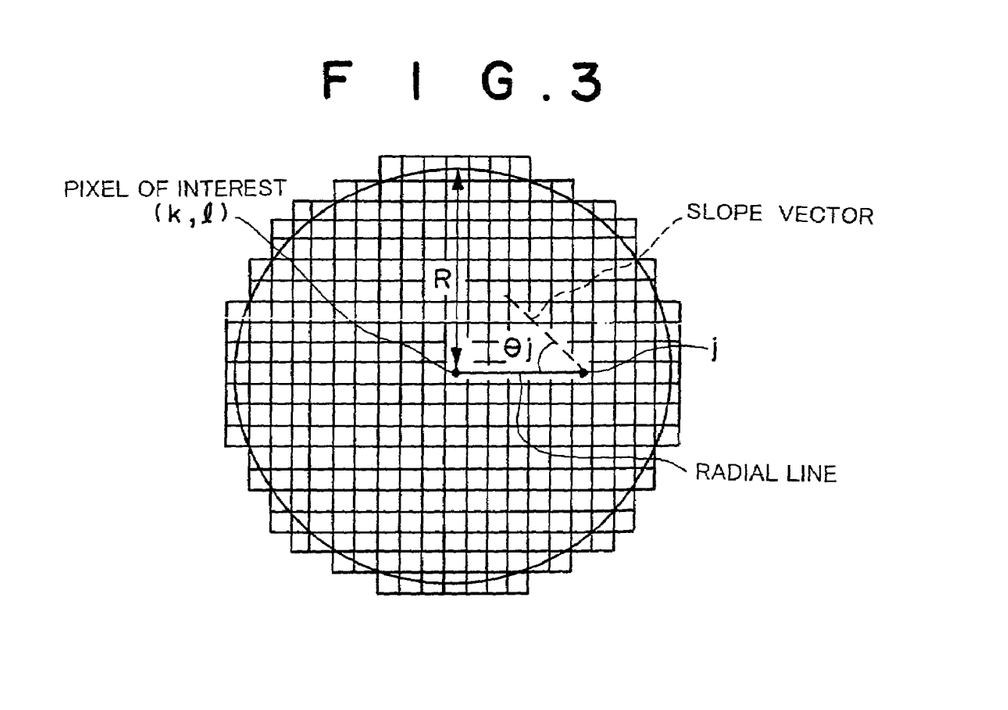
FIG. 3 is a drawing provided for explaining the angle formed between the linear line connecting the pixel of interest with each pixel j and the slope vector within the pixel j.

In the equation (2), N represents the number of pixels within a circle having a radius R centered on a pixel of interest, and θ is the angle formed between the slope vector computed according to aforementioned equation (1) and the linear line connecting the pixel of interest located at the center of said circle and each pixel j within said circle (see FIG. 3). Accordingly, the concentration C computed according to aforementioned equation 2 becomes a large value when the slope vector of each pixel points toward the pixel of interest.

The slope vector of a pixel j would point substantially to the center of the shadow regardless of the degree of contrast of the shadow, if the pixel j resided near the shadow of the tumor. Thus, it can be assumed that a pixel of interest for which the concentration C is of a large value would be a pixel near the center of the shadow of the tumor. On the other hand, because the slope vectors within the shadow of a blood vessel or other elongated shadow tend to have substantially parallel directions, the concentration C thereof is small. Accordingly, the shadow of the tumor can be appropriately detected by calculating the value of the concentration C for each pixel constituting the image to be analyzed taking that pixel as the pixel of interest and thereafter checking whether or not the calculated value of the concentration C is larger than the predetermined threshold value. As described above, the iris filter is less likely to erroneously detect the shadow of a blood vessel, a mammary gland, etc. than a regular differential filter, and thus has the advantage of detecting the shadow of a tumor more effectively.

Figure 4:
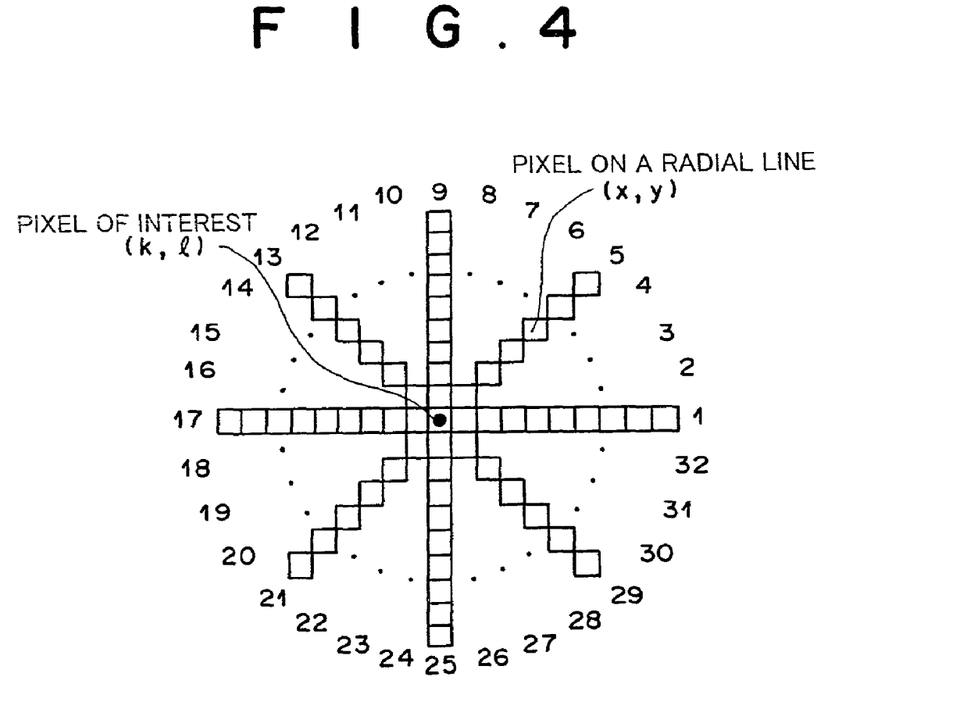
FIG. 4 illustrates the concept of an iris filter capable of changing the size and shape of the active portion thereof flexibly.

The iris filter used in the actual detection process is preferably configured so that the size and shape of an actual portion thereof may be arbitrarily changed to maintain stable detection capability regardless of the size and shape of the tumor. FIG. 4 shows an example of such a filter, which is different from that shown in FIG. 3. The filter shown in FIG. 4 evaluates the values of the concentration C only for those pixels on predetermined lines extending radially from the pixel of interest. The angle between any two adjacent radial lines is 2π/M degrees, wherein M represents the number of radial lines. In FIG. 4, M=32 is assumed, and thus the angle between any two adjacent lines is 11.25 degrees.

A set of coordinates ([x], [y]) for the nth pixel on the ith radial line is given by the following equations (3) and (4):

$$x = k + n \cos\{2\pi(i-1)/M\} \quad (3)$$

$$y = l + n \sin\{2\pi(i-1)/M\} \quad (4)$$

wherein the coordinates of the pixel of interest are designated as (K,l), and the coordinates [x], [y] are the largest integers that do not exceed the values of the coordinates x, y, respectively.

The concentration of the slope vectors within the first n pixels on a radial line i toward the pixel of interest is obtained for several values of n, and the maximum value thereof, Cimax, is selected on a line-by-line basis. Then, the average value of Cimax over every radial line i is taken as the concentration C of the slope vectors toward the pixel of interest.

More specifically, the concentration $Ci(n)$ is first obtained for several values of n using the following equation (5):

$$Ci(n) = \sum_{i=1}^{n} \{(\cos\theta_{ij})/n\}, \; Rmin \leq n \leq Rmax \quad (5)$$

Derived from the equation (5) is the concentration of the slope vectors within the first n pixels on a radial line i toward the pixel of interest, taking one integer within the range of Rmin≤n≤Rmax as the value of n.

Herein, Rmin to Rmax stand for the minimum radius and the maximum radius for the suspected shadow of the tumor.

Based on each value of Ci(n) calculated using the equation (5), the concentration C of the slope vectors toward the pixel of interest is computed using the following equations (6) and (7):

$$Ci_{\max} = \max_{Rmin \leq n \leq Rmax} Ci(n) \quad (6)$$

$$C = (1/32) \sum_{i=1}^{32} Ci_{\max} \quad (7)$$

As each Cimax obtained using the equation (6) is the maximum value of the concentration Ci (n) (Rmin≤n≤Rmax) obtained for the radial line i using the equation (5), the dimension between the pixel of interest and the pixel for which the Ci (n) thereof has been selected as Cimax may be considered as a radius of the suspected shadow of the tumor in the direction of the radial line.

The periphery of the suspected anomalous shadow of the tumor is defined by a set of straight lines or non-linear curves connecting each pixel having the concentration Ci thereof selected as the Cimax on each radial line i (i.e., I=1, 2, . . . , 32).

Then, by using equation (7), the concentration C of the slope vectors toward the pixel of interest is obtained by taking the average value of Cimax over every radial line i (herein, the number of radial lines is 32). This concentration C would be the output value I of the iris filter. Then the output value I of the iris filter is compared to the predetermined threshold value T. If I≧T (or I>T), the area centering on that pixel of interest would remain as the suspected shadow of a tumor, and if I≦T (or I<T), the area would be regarded as a normal area, and another candidate area would be searched for.

In the above process, the following equation (5') for calculating each Ci(n) may substitute for the equation (5).

$$Ci(n) = \frac{1}{n - Rmin + 1} \sum_{i=Rmin}^{n} \cos\theta_{ij}, \; Rmin \leq n \leq Rmax \quad (5')$$

Taking one integer within the range of Rmin≤n≤Rmax as the value of n, the concentration of the slope vectors within Rminth to nth pixels on a radial line i toward the pixel of interest is obtained by the equation (5').

That is to say, equation (5') computes concentration Ci(n) within an area defined by utilizing the pixel corresponding to the shortest radius Rmin of the radius of the suspected anomalous shadow of a tumor for which a detection is being performed as the starting point, and a point in the range from Rmin to Rmax as the finishing point.

On the other hand, a morphology filtering process is a process for detecting suspected microcalcification shadows, which, like the shadow of a tumor, is a characteristic feature of breast cancer. The morphology filtering process determines the suspected microcalcification shadows based on the use of a multiscale λ and a structural factor (a mask) B, and is advantageous in that: (1) the process is effective in extracting the shadows that are in fact shadows of microcalcifications; (2) the process is less susceptible to producing erroneous readings due to effects caused by complex background information; and (3) the extracted images of microcalcifications are free from distortion, etc. That is to say, microcalcification shadows detected using the morphology filtering process reflect geometric features (e.g., the size, shape, or image density distribution) of the actual microcalcification shadows more precisely than those shadows detected by using general differentiation processes. A general outline of the steps constituting a morphology filtering process will be given below.

Basic Morphology Calculation

A process of morphology generally consists of a series of set operations in an N-dimensional space. However, the process explained hereunder is directed to a two-dimensional monotone image for the sake of simplicity.

The two-dimensional monotone image is regarded as a three-dimensional space constituted of a certain number of coordinate points, (x, y), having respective heights corresponding to an image density signal f(x, y) thereof. In the present description, an image density signal f(x, y) of a higher level represents higher brightness, i.e., lower image density.

Now, for further simplicity, a linear function f(x) corresponding to the image density signal along a strip of the image will be considered. A structuring element used in the morphology calculation is a symmetric function with respect to the zero-point, i.e., $$g^S(x) = g(-x) \quad (8)$$

Wherein the value is equal to 0 within a defined domain, said domain being:

$$G = \{-m, -m+1, \ldots, -1, 0, 1, \ldots, m-1, m\} \quad (9)$$

Using the above structuring element g, basic forms of morphology operations can be written in quite simple forms as shown below.

dilation: $[f \oplus G^S](i) = \max\{f(i-m), \ldots, f(i), \ldots, f(i+m)\}$ (10)

erosion: $[f \ominus G^S](i) = \min\{f(i-m), \ldots, f(i), \ldots, f(i+m)\}$ (11)

opening: $f_g = (f \ominus g^S) \oplus g$ (12)

closing: $f^g = (f \oplus g^S) \ominus g$ (13)

Figure 5A:
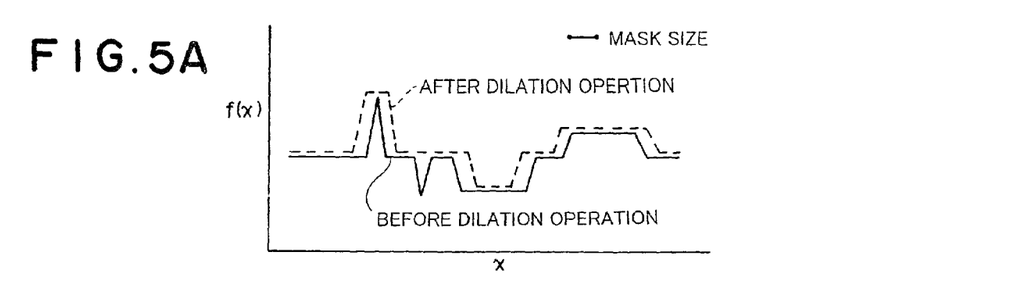
FIGS. 5A to 5D are diagrams each illustrating the concept of one of the basic of the morphology operations.
Figure 5B:
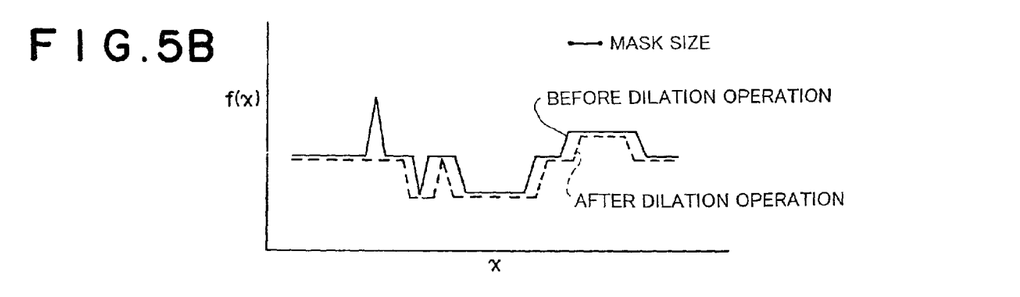
Figure 5C:
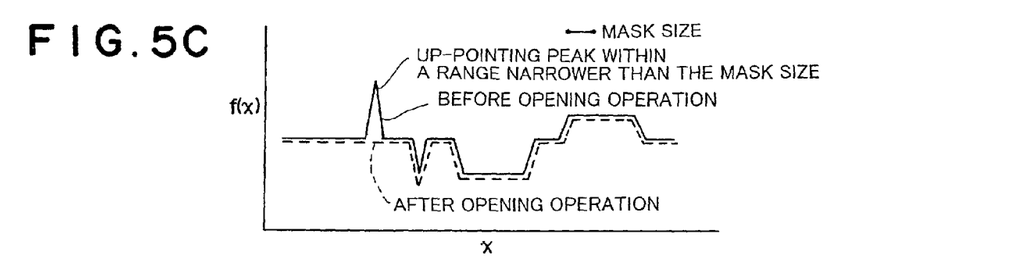
Figure 5D:
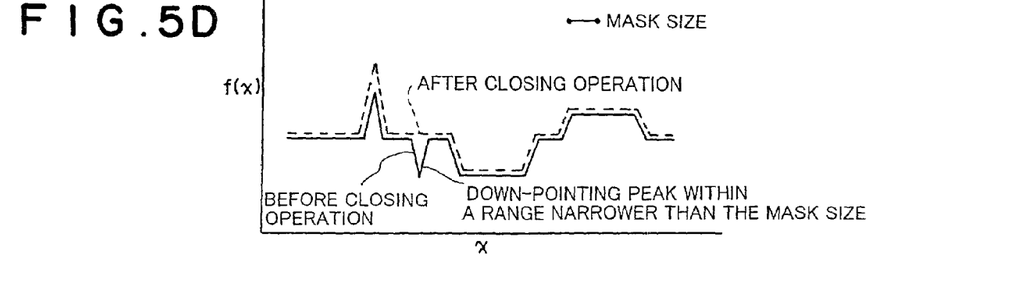

Herein, the dilation operation is an operation of searching for the maximum value within a range of ±m (a value determined by structural element B), centered on a pixel of interest (see FIG. 5A). The erosion operation is an operation of searching for the minimum value within a range of ±m centered on a pixel of interest (see FIG. 5B). The opening operation is an operation of searching for the minimum value first and then searching for the maximum value. The closing operation is an operation of searching for the maximum value first and then searching for the minimum value. More specifically, the opening operation smoothes the image density distribution on the low-brightness side thereof to filter out up-pointing peaks, (i.e., those parts with higher brightness and thus lower image density than adjacent areas thereof) which occur within a range spatially narrower than the present example (see FIG. 5C). The mask size is 2 meters in the present example. On the other hand, the closing operation smoothes the image density distribution on the high-brightness side thereof to filter out down-pointing peaks (i.e., those parts with lower brightness and thus higher image density than adjacent areas thereof) which occur within a range spatially narrower than a mask size of 2 m (see FIG. 5D).

For cases in which the image signal f(x, y) of higher level represents higher image density, because the size relationship between the image density value f(x) and the image signal would be reversed from the case in which the higher the brightness, the higher the signal, the dilation operation would be the operation identical to the above-described erosion operation (see FIG. 5B) and the erosion operation would be the operation identical to the above-described dilation operation (see FIG. 5A). Similarly, the opening operation would be the operation identical to the above-described closing operation (see FIG. 5D) and the closing operation would be the same operation identical to the above-described opening operation (see FIG. 5C). In the following descriptions, however, as well as in the above description of the morphology filtering process, the image density signal f(x, y) of higher level is assumed to represent higher brightness.

Application to Calcification Shadow Detection

There has been a conventional subtraction method for detecting a calcification shadow in which a smoothed image is subtracted from an original image. However, a simple smoothing method is incapable of precisely distinguishing a calcification shadow from an elongated normal shadow (e.g., a shadow of a mammary gland, a mammary gland support tissue, a blood vessel, etc.). To overcome this problem a morphology operation represented by the following equation (14), which is based on an opening operation using a structuring element B, was proposed in Obata's papers, each titled "Extraction of Microcalcifications on Mammogram Using Morphological Filter with Multiple Structuring Elements" (Electronic Information Communication Society Journal, D-II, Vol. J75-D-II, No. 7, p. 1170–1176, 7/1992) and "Basics of Morphology Operation and its Application to Mammogram" (Medical Imaging Technology, Vol. 12 No. 1, 1/1994).

$$P = f - \max_{i \in (1, \ldots, M)} \{(f \ominus Bi) \oplus Bi\} \quad (14)$$

$$= f - \max_{i \in (1, \ldots, M)} \{f_{Bi}\}$$

Figure 6:
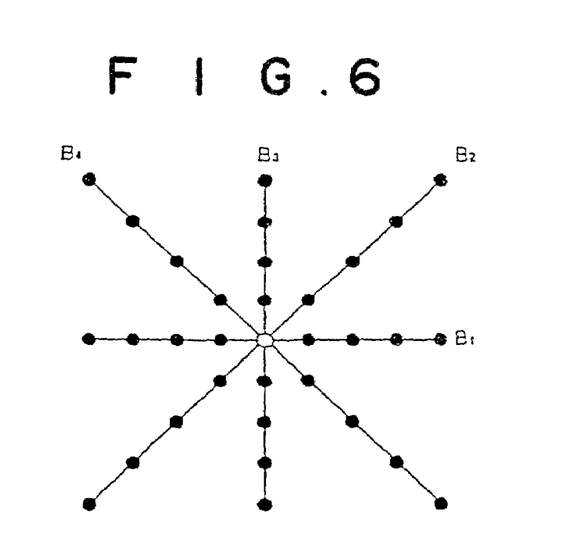
FIG. 6 shows a structuring element formed of four linear lines.

In the above equation (14), Bi(I=1, 2, 3, 4) represents one of the four linear dimensions of the structuring element B as shown in FIG. 6. When selecting lines longer than respective dimensions of the target calcification shadow as the linear dimensions Bi and conducting the opening operation, the target calcification shadow will be regarded as an up-pointing peak of the image density signal which is narrower in each direction corresponding to each Bi than the structuring element B and thus will be filtered out. On the other hand, an elongated normal shadow, which usually has a dimension longer than that of structuring element B in one or more directions corresponding to directions of Bi, still remains after the opening operation (i.e., the operation represented by the second term of the equation (14)). Accordingly, an image containing only those shadows strongly suspected to be calcification shadows will be derived by subtracting the smoothed image, which is obtained through the opening operation and contains no calcification shadow, from an original image f.

Note that for cases in which the image density signal f(x), y) of higher level represents higher image density, i.e., where the closing operation is used in place of the opening operation, the following equation (15) may substitute for the equation (14).

$$P = f - \min_{i \in \{1,...,M\}} \{(f \oplus Bi) \ominus Bi\}$$
$$= f - \min_{i \in \{1,...,M\}} \{f_{Bi}\} \quad (15)$$

However, the operation represented by equation (14) or (15) cannot eliminate a normal shadow having a size substantially the same as that of the target calcification shadow. Thus, the additional morphology calculation described by equation (16) is carried out to obtain differential data Mgrad used for eliminating such small normal shadows.

$$M_{grad} = (1/2) \times \{\oplus \lambda B - f \ominus \lambda B\} \quad (16)$$

As a spot having larger value of Mgrad is more likely to be a calcification shadow, a suspected calcification shadow may be determined using the following criteria.

IF $P(i,j) \geq T1$ and $M_{grad}(i,j) \geq T2$ (17)

Then $Cs(i,j)=P$ else $Cs(i,j)=0$

In the above equation (17), T1 and T2 represent threshold values predetermined empirically.

However, for cases in which the size of the normal shadow is different from that of the target calcification shadow, because the normal shadow can be eliminated by performing only a comparison of the P of the equation (14) and the predetermined threshold value T1, it is sufficient that only the first criterion of the equation (17) (P (i, j)≧T1) be satisfied for cases in which there are no normal shadows having the same size as the target calcification shadow remaining.

Finally, as shown in the equation (18), by combining the multiscale opening and closing calculations, microcalcification clusters Cc are detected.

$$C_c = C_S \oplus \lambda_1 B \ominus \lambda_3 B \ominus \lambda_2 B \quad (18)$$

In the above equation (18), λ1 and λ2 are determined by the greatest distance between the microcalcification shadows that are desired to be fused, and the largest radius of isolated microcalcifications shadows that are desired to be eliminated, respectively, and λ3=λ1+λ2.

Note that as described above, the explanation relating to the morphology filters has been conducted for a case in which high-brightness, high signal level image data has been the subject of processing, however, for cases in which the image data to be processed is high-density, high signal level image data (image data having higher digital values as the density of the pixels are higher), the relationship between the opening calculation and the closing calculation is reversed.

When an anomalous shadow detection processing system is introduced into a hospital or other facility, the detection threshold values (detection parameters) T, T1 and T2 utilized in performing the above-described morphology processing and anomalous shadow detection processing are experimentally determined and set in advance as initial values.

However, because the detection results obtained by use of the anomalous shadow detection processing system described above are susceptible to fluctuations due to factors in the image-obtaining environment of said facility, if the detection parameters are set as particular values, there is a possibility that the results obtained will vary for each facility. Therefore, when introducing an anomalous shadow detection processing system, in order to facilitate stable detection capacity across all facilities in which such systems are in use, it is necessary that the detection parameters are matched to the image-obtaining environment of each facility and set.

SUMMARY OF THE INVENTION

The present invention has been developed in consideration of the circumstances described above, and it is a primary object of the present invention to provide a suspected anomalous shadow detection method and a detection processing system possible of attaining stable detection capacity at all facilities into which the system is to be introduced, unimpeded by the conditions of the image-obtaining environment of each facility.

The method of detecting suspected anomalous shadows according to the present invention comprises the steps of: obtaining the radiation-image data representing a radiation image that has been obtained of a an examination area of a subject (hereinafter referred to as a target subject) by an image obtaining means; and based on said obtained radiation-image data, detecting suspected anomalous shadows contained within said radiation image by performing an anomalous shadow detection process utilizing a predetermined detection parameter; further comprising the steps of obtaining phantom-image data representing a radiation image of a standard-phantom obtained by an image obtaining means for obtaining a radiation image of a standard-phantom having a shadow pattern formed of a plurality of evaluative models each of which corresponds to a different detection capability level; outputting the obtained phantom-image data by an outputting means; and setting a detection parameter based on the threshold value obtained based on an evaluation of the image quality of the outputted phantom-image data.

Here, "an anomalous shadow detection process" refers to an iris filtering process for detecting the suspected anomalous shadow of a tumor, a morphology process for detecting anomalous microcalcification shadows, etc.; in short, any type of process utilizing a detection parameter and which is performed in order to detect other types of anomalous shadows appearing in a radiation image qualifies.

Further, "detection parameter" refers to a parameter that changes the detection capacity; the threshold value T occurring in the iris filtering process, and the threshold values T1 and T2 occurring in the morphology process are such parameters.

Figure 9:
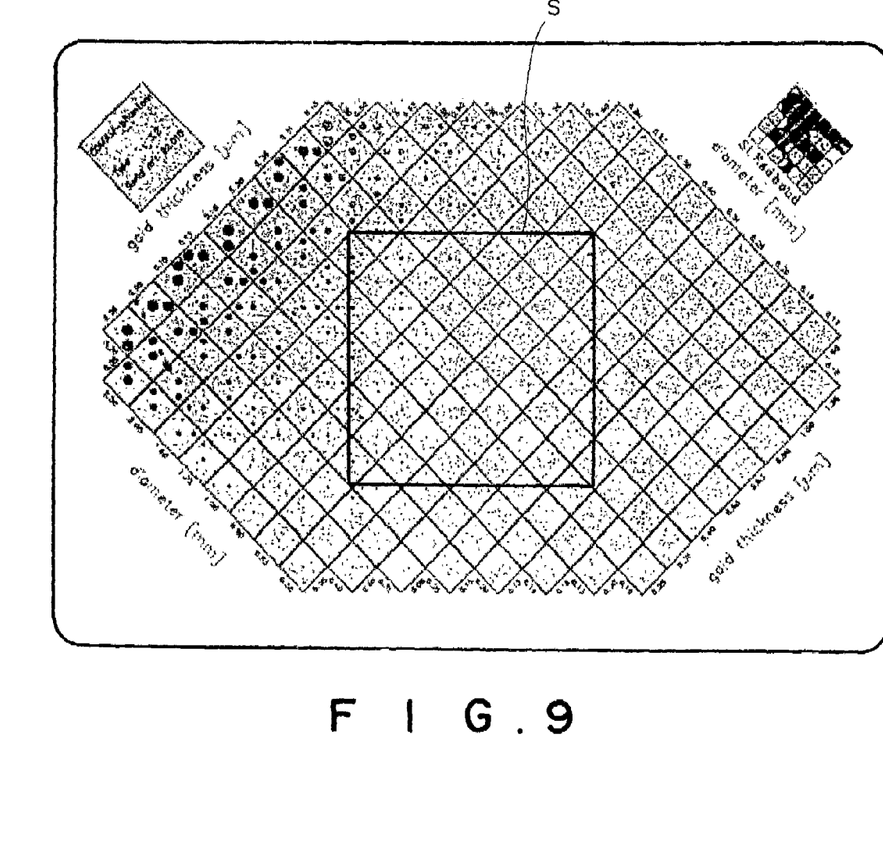
FIG. 9 shows a CDMAMMO phantom.

Still further, "a shadow pattern formed of a plurality of evaluative models each of which corresponds to a different detection capability level" refers to a shadow pattern formed of a plurality of evaluative models, each corresponding to one of a detection capability level from among a plurality of detection capability levels: For example, as shown in 12–16 of FIG. 7, a pattern of the shadows cast by tumors formed of a plurality of evaluative models modeled on a plurality of tumors differing in size; as shown in 7–11 of FIG. 7, a microcalcification shadow pattern formed of a plurality of evaluative models modeled on a plurality of microcalcification shadows, each point of which is of a different size (contrast); and as shown in FIG. 9, a shadow pattern formed of an evaluative model having a plurality of contrast gradients. Note that other than the patterns described above, various types of patterns, corresponding to the characteristic features of targeted anomalous shadows, can be used.

In addition, "outputting means" refers to a printer or other printing means, a CRT or other image displaying means, in addition to a means for outputting phantom-image data to a means for detecting suspected anomalous shadows within an image, based on image data, etc.

Note that application of this method is particularly effective when the subject to be examined is a breast.

A first suspected anomalous shadow detection system according to the present invention comprises: an image obtaining means for obtaining a radiation image of a target subject; a radiation-image data obtaining means for obtaining the radiation-image data of the radiation image of the target subject obtained by the image obtaining means; and an anomalous shadow detecting means for detecting suspected anomalous shadows contained within said radiation image by performing an anomalous shadow detection processing utilizing a predetermined detection parameter; wherein, the anomalous shadow detecting means determines a threshold value so as to enable the detection and obtainment of an evaluative model corresponding to a desired detection capability level based on a phantom-image data representing a standard phantom-image having at least one type of anomalous shadow pattern formed of a plurality of evaluative models each of which corresponds to a different detection capability level, and automatically setting a detection parameter based on the threshold value obtained thereby.

Here, the referent of "radiation-image data obtaining means" can include an image readout means for reading out the radiation-image data of the radiation image obtained by the image obtaining means, an obtaining means utilizing a fixed sensor, etc. for directly converting X-rays to image data, etc.

Further, the referent of "anomalous shadow pattern" can include a pattern of the shadow of a tumor, in which the substantially circular perimeter is displayed as an unclear image and the degree of brightness becomes progressively higher approaching toward to the center from said perimeter, a microcalcification shadow pattern represented by an image in which a plurality of points are gathered, and any pattern that represents a model of the shape of an anomalous shadow.

Note that it is desirable that at least one of the anomalous shadow patterns from among those included in the standard phantom is a pattern of a microcalcification shadow or a pattern of the shadow of a tumor.

Further, according to the suspect anomalous shadow detection process, a morphology filtering process for detecting microcalcifications and an iris filtering process for detecting an anomalous shadow of a tumor can be employed.

Another suspected anomalous shadow detection system according to the present invention comprises: an image obtaining means for obtaining a radiation image of a target subject; a radiation-image data obtaining means for obtaining the radiation-image data of the radiation image of the target subject obtained by the image obtaining means; and an anomalous shadow detecting means for detecting suspected anomalous shadows contained within said radiation image by performing an anomalous shadow image process utilizing a predetermined detection parameter; further comprising a parameter setting means for automatically setting a detection parameter based on the radiation-image data of a predetermined target subject obtained by the radiation-image data obtaining means of the radiation image obtained by the image obtaining means.

Here, a standard phantom-image having a shadow pattern formed of a plurality of evaluative models, each of which corresponds to a different detection capability level, can be applied as the predetermined target subject. The standard phantom applied in this case can be a standard phantom having a pattern of an anomalous shadow, a standard phantom having a surface texture pattern having a plurality of contrast gradations, etc. Further, aside from the patterns described above, various types of shadow patterns, depending on the characteristic features of the targeted anomalous shadow, can be used.

Further, aforementioned predetermined target subject is not limited to being a target subject having a predetermined shape. That is to say, the image obtaining means obtains an image without specifying a target subject (hereinafter referred to as "beta" image obtainment), and the radiation-image data obtained thereby can serve as aforementioned radiation image data of a predetermined subject.

Still further, the parameter setting means can be a means for computing a correction value for the granularity and/or contrast of an image based on the granularity and/or contrast of the radiation-image data of a predetermined target subject, and setting a value for the detection parameter based on said correction value for the granularity and/or contrast.

Note that the referent of "detection parameter" can include the threshold value T occurring in the iris filtering process, the threshold values T1 and T2 occurring in the morphology filtering process, and various other parameters utilized when detecting suspect anomalous shadows that change the detection capacity thereof.

According to the method and processing system of the configuration described above for detecting suspected anomalous shadows according to the present invention, the image quality of the image data of a standard phantom, etc. obtained by the image obtaining means of each facility into which the system is introduced is evaluated for each facility, because the value of the detection parameter to be used at said each facility is set based upon the results of said evaluation, it becomes possible to set the detection parameter so that the same detection result is obtained across all of said facilities, and stable detection capability can be obtained regardless of differences between the image obtaining environments of said facilities.

Note that the efficacy of the present invention in stabilizing detection performance with respect to the influence of differences in image obtaining environments is particularly high for cases in which the target subjects are breasts.

DESCRIPTION OF THE PREFERRED EMBODIMENTS

Figure 8:
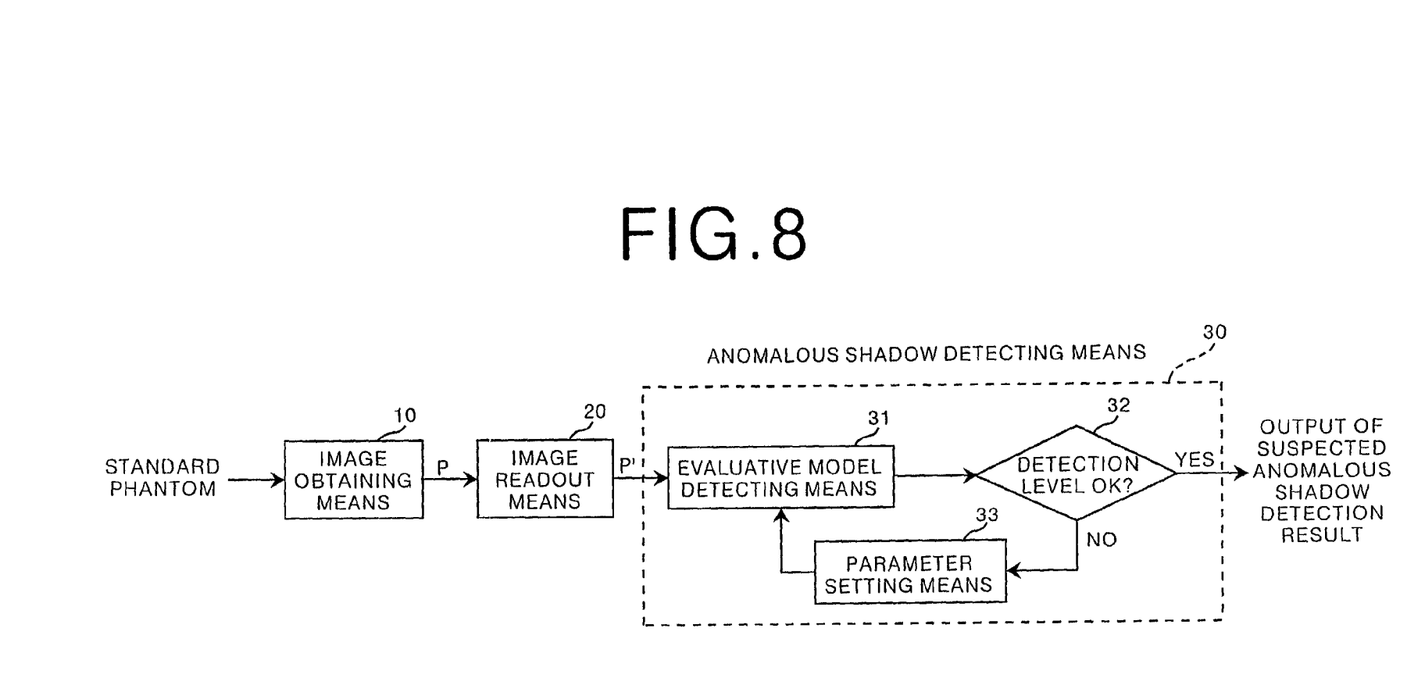
FIG. 8 is a schematic drawing of the configuration of an embodiment of the suspected anomalous shadow detection system according to the present invention.

Hereinafter, an embodiment of the suspected anomalous shadow detection system according to the present invention will be explained referring to the attached drawings. FIG. 8 is a schematic drawing of an embodiment of the suspected anomalous shadow detection system according to the present invention.

The current embodiment of the suspected anomalous shadow detection system comprises an image obtaining means 10 for obtaining a phantom image P, an image readout means 20 (radiation-image readout means) for obtaining phantom-image data P' of the phantom image P obtained by the image obtaining means 10, and an anomalous shadow detecting means 30 into which the phantom-image data P' obtained by the image readout means 20 is input and which detects an evaluative model of an anomalous shadow contained within the phantom image P of the standard phantom based on the phantom-image data P'.

Figure 7:
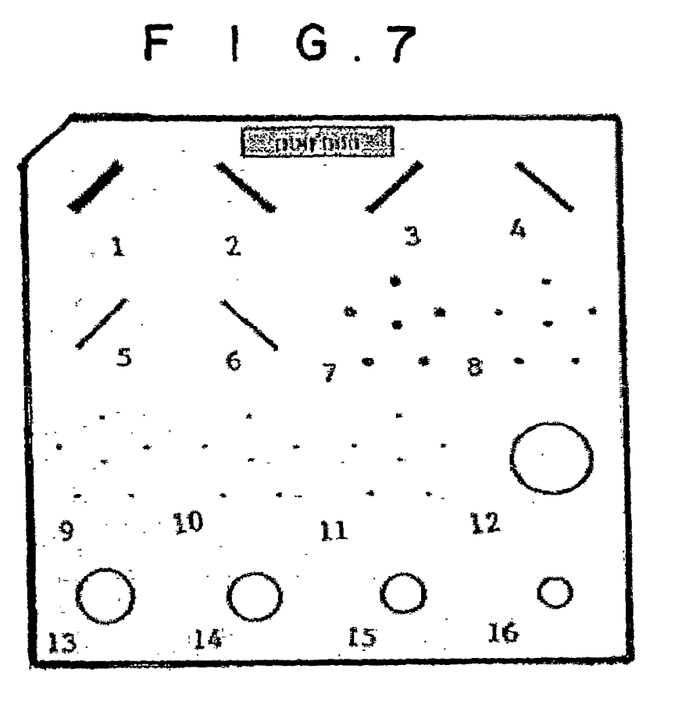
FIG. 7 shows an RMI phantom.

An RMI phantom provided with patterns of the shadows of tumors (12–16) and patterns of microcalcification shadows (7–11) is used as the standard phantom (see FIG. 7). Each pattern of anomalous shadows is formed by evaluative models, each of which has a different level of detection capability. That is to say, the pattern of the shadows of a tumor becomes harder to detect as the size of the substantially circular model becomes smaller; likewise, the pattern of a microcalcification shadow becomes harder to detect as the size of the points forming the pattern becomes smaller (the contrast becomes weak); therefore, "evaluative models, each of which has a different level of detection capability" refers to models for each of the shapes of the different types of targeted anomalous shadows, and represents different sizes thereof. Note that 1–6 of FIG. 7 represent the patterns of the elongated shadows of mammary glands, etc., and are not utilized in the current embodiment.

The image obtaining means 10 and the image readout means 20 are installed in a hospital or other facility, and both are integrated into a single apparatus that carries out the obtaining and reading out of an image of a target subject, which are breasts and the like. Generally, the anomalous shadow detecting means 30 detects the suspected anomalous shadows contained in the entire image based on the image data of a target subject such as mammary glands, etc. input thereto .

The phantom-image data P' obtained by the image readout means 20, is input to the anomalous shadow detecting means 30 which is provided with an evaluative model detecting means 31 for detecting, based on the phantom-image data P', evaluative models contained within the radiation-image P of the standard phantom, an evaluating means 32 into which is input the result obtained by the evaluative model detecting means 31, that compares said result to a predetermined detection level parameter and performing an evaluation thereof, and a parameter setting means 33 for resetting the detection parameter based on a predetermined rule when the result of the evaluation performed by the evaluating means 32 indicates that the detection level of the evaluative model differs from a desired value. Note that for cases in which the result of the evaluation performed by the evaluating means 32 indicates that the detection level of the evaluative model detected by the evaluative model detecting means 31 is at a desired detection level, the detection parameter is not reset by the parameter setting means 33.

Here, the referent of "detection parameter" can include the threshold value T occurring in the iris filtering process, and the threshold values T1 and T2 occurring in the morphology filtering process; a particular value is set as the initial value for this parameter.

Next, the operation (detection method) of a suspected anomalous shadow detection system of the configuration described above according to the current embodiment will be explained.

The image obtaining means 10 obtains a radiation image of the standard phantom.

The image readout means 20 reads out the phantom image P obtained of the standard phantom by the image obtaining means 10, and obtains a phantom-image data P'.

The evaluative model detecting means, into which the phantom-image data P' obtained by the image readout means 20 is input, detects, by performing an anomalous shadow detection process, the anomalous shadow patterns (evaluative models) contained within the phantom-image P. At this point, the patterns of the shadows of tumors contained within the standard phantom image are detected by the iris filtering process, and the microcalcification shadows contained within the standard phantom image are detected by the morphology filtering process. Note that the evaluative model detecting means 31 remembers the phantom-image data P inputted thereto, and after detecting the evaluative models, stores said phantom-image P.

The evaluating means 32, into which is input the detection result data from the evaluative model detecting means 31, compares said data to a preset desired detection level. If the detection result has not attained the desired detection level, the detection result data and data indicative of the desired detection level are output to the parameter setting means 33. Note that for cases in which the detection result of the evaluative model detecting means 31 is the same as that of the desired detection level, the parameter setting process is complete, and the detection result is output.

The parameter setting means 33, into which is input the detection result data from the evaluating means 32 and data indicative of the desired detection level, changes the value of the detection parameter based on said data, and resets the detection parameter of each anomalous shadow detection process occurring in the evaluative model detecting means 31 to said changed value. For example, for a case in which the detection level for the shadow of a tumor is set at 2 (the detection levels for two patterns of the shadows of tumors (12, 13) occurring in the standard phantom), and the evaluative result of the detection level from the evaluative models was 1 (a level for detecting evaluative model (12) only), the value of detection parameter T (threshold value) for the iris filtering process occurring in the evaluative model detecting means 31 is lowered one step and reset thereat as a new value. Likewise, if the desired detection level for microcalcification shadows is 2, and the evaluative result from the evaluative model was 1, the value of detection parameter (threshold value) T1, T2 are lowered one level, and set thereat as a new value. Note that the level to which the detection parameter is lowered (or, raised) is set based on a predetermined rule set in advance according to the characteristics of each suspected anomalous shadow detection process.

After the new value of the detection parameter has been set, the evaluative model detecting means 31 again subjects the phantom-image P stored therein to the anomalous shadow detection process and re-detects the evaluative models contained therein.

The evaluating means 32, the parameter setting means 33 and the evaluative model detecting means 31 perform the same processing as described above for the detection result obtained of by said re-detecting, and the process described above is repeated until the detection result obtained by the evaluative model detecting means 31 is the same as that of the desired detection level.

According to the suspected anomalous shadow detection method and system of the current embodiment, because by automatically setting of a value for the detection parameter it becomes possible to adjust the detection capacity of the system, the systems installed at each facility can be adjusted not only when said systems are installed, but at regular intervals as well. That is to say, it is always already possible to obtain a stable detection result by simply readjusting the system, which is also effective for QC of the anomalous shadow detection system itself.

As to the standard phantom, aside from aforementioned RMI phantom, so long as a plurality of evaluative models corresponding to the detection capability levels of the anomalous shadows that are the object of a detection process are provided, any of a number of options can be used.

Next, another embodiment of the system for detecting suspected anomalous shadows according to the present invention will be explained. According to the suspected anomalous shadow detection method of the current embodiment, the phantom-image data P' obtained by the image readout means 20 is output to an X-ray film, etc. by an output apparatus, and the value of the detection parameter is reset manually based on the level of visual recognizability of the output result thereof. For example, if the desired detection level is 2 and the level of visual recognizability is 1, the initial value of the detection parameter is, for example, lowered to ½ thereof and set thereat, and the operation of the system is started in the state in which the desired detection level has been obtained. Note that it is assumed that adjustments have been made to correct for variations in the image quality of the output apparatus occurring at each facility, and that there is no effect attributable thereto with respect to the evaluation result of the visual recognizability level.

Note that according to the embodiment described above, in which the image resulting from the output of the image data to X-ray film, etc. is subjected to a visual recognizability check of the image quality thereof, said output image is not necessarily limited to being a phantom having a pattern of anomalous shadows; it is possible to employ a phantom having various shadow patterns formed of a plurality of evaluative models corresponding to a plurality of different detection capability levels. For example, if the anomalous shadow to be detected is a microcalcification shadow, a CDMAMMMO phantom (see FIG. 9) can be used. The term "CDMAMMMO phantom" refers to a phantom capable of producing a fairly detailed analysis relating to an evaluation of the contrast.

Note that aside from the iris filtering process and the morphology filtering process described above, the suspected anomalous shadow detection process can consist of any suspected anomalous shadow detection process in which the detection capacity is capable of being changed by the detection parameter.

Figure 10:
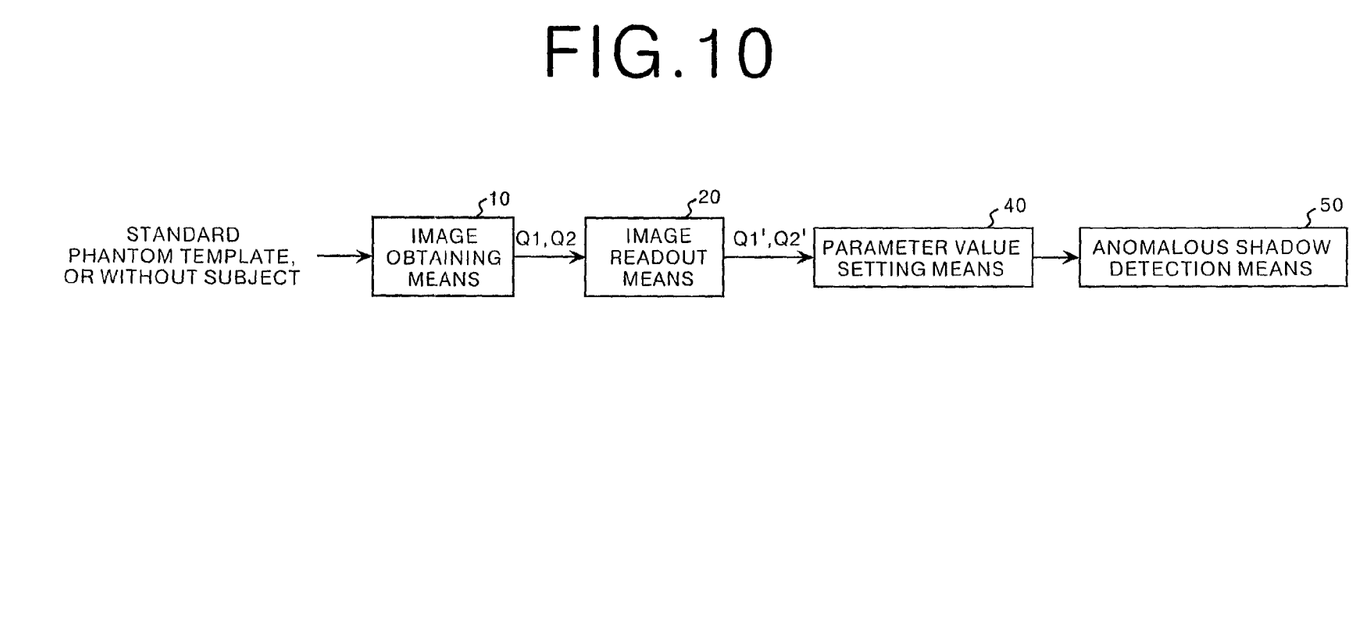
FIG. 10 is a schematic drawing of the configuration of another embodiment of the suspected anomalous shadow detection system according to the present invention.

Next, another embodiment of the system for detecting suspected anomalous shadow according to the present invention will be explained. FIG. 10 is a schematic drawing of the configuration of the suspected anomalous shadow detection system according to the current embodiment. Note that elements that are the same as those of the embodiment shown in FIG. 8 are likewise labeled, and insofar as it is not particularly required, further explanation thereof has been omitted.

The current embodiment of the suspected anomalous shadow detection system comprises an image obtaining means 10 for obtaining a radiation image, an image readout means 20 (radiation-image readout means) for obtaining image data Q' of an image Q obtained by the image obtaining means 10, a parameter setting means 40, into which is input the phantom-image data P' obtained by the image readout means 20, that computes a correction value for the detection parameter occurring in the anomalous shadow detection process, and based on the result of said computation, sets the value of the detection parameter at the anomalous shadow detecting means 50.

The anomalous shadow detecting means 50 inputs the image data of a target subject such as a breast, etc., and based on said image data, detects the suspected anomalous shadows contained within the image by performing an anomalous shadow detection process utilizing a predetermined detection parameter (threshold value).

Further, the parameter setting means 40 of the current embodiment computes a correction value for the granularity and contrast of the detection parameter, based on the granularity and the contrast of the image data Q' input thereto from the image readout means 20, and sets the sums resulting from the addition of both of these two correction values to each of the basic threshold values T1 and T2 of the morphology filtering process, as the values of the detection parameter.

Next, the operation of a suspected anomalous shadow detection system of the configuration described above according to the current embodiment will be explained.

If the image obtaining means 10 obtains a CDMAMMMO phantom image of a CDMAMMMO phantom at a standard number of lines (such as 15 mR) as well as a "beta" image thereof, the CDMAMMMO phantom image Q1 and the "beta" CDMAMMMO phantom image Q2 from the image obtaining means 10 are input to the image readout means 20 which, by a predetermined standard method, obtains a CDMAMMMO phantom image data Q1' and a "beta" CDMAMMMO phantom image data Q2'.

The CDMAMMMO phantom image data Q1' and the beta CDMAMMMO phantom image data Q2' from the image obtaining means 20 are input to the parameter setting means 40, which computes a granularity correction value based on the "beta" CDMAMMMO phantom image data Q2' and a contrast correction value based on the CDMAMMMO phantom image data Q1' Hereinafter, the method of deriving each correction value will be more specifically explained.

When the granularity correction value is computed based on the "beta" CDMAMMMO phantom image data Q2', the RMS value (the average volume of noise) of a predetermined region (e.g., a 10 cm×10 cm region of the central section) of the central section of the image is computed. The RMS value is the granularity, that is, a value that represents the volume of noise produced by the imaging system of each facility, represented by the following equation:

$$\text{RMS value} = \sqrt{\sum_i \sum_j (X_{ij} - \hat{X})^2}$$

$\hat{X}$ is the mean value of $X_{ij}$, $X_{ij}$ is the pixel value of the image data The RMS value becomes large when the volume of noise is high, and small when the volume of noise is low. Using the RMS value, the granularity correction value K1 is derived according to the following equation:

$$K1 = (\text{RMS value}/A - 1.0) \times \alpha$$

wherein A and α are constants: for example, A=0.806, α=0.4, etc. Note that the granularity correction value K1 is determined experimentally based on a 10 bit image data.

On the other hand, when the contrast correction value K2 is computed based on the CDMAMMMO phantom image data Q1', a microcalcification image CS is obtained utilizing the above described morphology filtering process for a predetermined region S of the central section of the image (see FIG. 9), and the sum of the signal value of the microcalcification image CS is computed. Using the signal value of the microcalcification image CS, the contrast correction value K2 is derived according to the following equation:

$$K2 = (\text{total sum}/B - 1.0) \times \beta$$

wherein B and β are constants: for example, B=140, β4.0, etc. The contrast correction value K2, like the granularity correction value K1, is determined experimentally based on a 10 bit image data.

The parameter setting means 40 sets as the detection parameters for the anomalous shadow detecting means 50 the sums resulting from the addition of the granularity correction value K1 and the contrast correction value K2 to each of the basic threshold values (preset threshold values to be determined experimentally) T1 and T2 occurring in the morphology filtering process.

Note that in the explanation of the current embodiment, an example has been given wherein the granularity correction value K1 and the contrast correction value K2 have been added to each of the basic threshold values T1 and T2 occurring in the morphology filtering process; however, it is also possible according to the current embodiment to obtain only one of either of the two correction values and add said obtained correction value to each of said values T1 and T2. Further, an example has been given wherein the CDMAMMMO phantom-image data Q1' is used when obtaining the contrast correction value K2; however, the current embodiment is not limited to the method given in said example: the pattern modeling the microcalcification shadow of the RMI phantom as shown in FIG. 7 can be used instead of the contrast correction value K2. In this case, evaluative models with a plurality of detection levels, from among the evaluative models of the microcalcification shadow of the RMI phantom are used. Further, an example has been given wherein the "beta" CDMAMMMO phantom-image data Q2' is used when obtaining the granularity correction value K1, however, the image data of the standard phantom can be used instead of the "beta" CDMAMMMO phantom-image data Q2'.

Further, the parameter setting process described above can also be adopted in a suspected anomalous shadow detection system provided with a determining means for determining after the suspected anomalous shadow detection processing by use of an iris filtering process, etc. has been performed, using the quantitative characteristics of the suspected regions of the detected anomalous shadows, etc., whether or not the suspected region are malignant or not.

Still further, the present invention is not limited to taking as subject images those produced by mammography CAD systems, the present invention can also be applied to chest CAD images, stomach cancer CAD images, and images obtained of various types of target subjects.

What is claimed is:

1. A method of detecting suspected anomalous shadows, comprising the steps of
    obtaining radiation-image data representing a radiation image obtained of a target subject by an image obtaining means,
    detecting, based on said obtained radiation image data, the suspected anomalous shadows contained within said radiation image by performing an anomalous shadow detection process utilizing a predetermined detection parameter, further comprising the steps of
    obtaining phantom-image data representing a radiation image obtained by said radiation image obtaining means of a standard phantom having a shadow pattern formed of a plurality of evaluative models each of which corresponds to a different detection level,
    outputting said obtained phantom image data by use of an output means, and
    setting as the value of the detection parameter a threshold value obtained by performing an image quality evaluation based on the phantom-image data outputted by the output means.

2. A method of detecting suspected anomalous shadows as defined in claim 1, wherein the target subject is a breast.

3. A system for detecting suspected anomalous shadows, comprising image obtaining means for obtaining a radiation image of a target subject,
    radiation-image data obtaining means for obtaining radiation-image data representing the radiation image obtained by said image obtaining means of the target subject,
    an anomalous shadow detecting means for detecting, based on the radiation-image data obtained by the radiation image data obtaining means, suspected anomalous shadows contained within the radiation image by performing an anomalous shadow detection process utilizing a predetermined detection parameter, wherein
    said anomalous shadow detecting means determines, based on a phantom-image data representing a standard phantom-image having at least one type of anomalous shadow pattern formed of a plurality of evaluative models each of which corresponds to a different detection capability level, a threshold value facilitating the detection and obtainment of an evaluative model corresponding to a desired detection capability level, and automatically sets the value of the detection parameter based on said threshold value.

4. A system for detecting suspected anomalous shadows as defined in claim 3, wherein
    at least one of the patterns of anomalous shadows contained in the standard phantom is the pattern of the shadows of tumors.

5. A system for detecting suspected anomalous shadows as defined in claim 3, wherein
at least one of the patterns of anomalous shadows contained in the standard phantom is the pattern of the shadows of microcalcifications.

6. A system for detecting suspected anomalous shadows as defined in any one of claim 3, 4, or 5, wherein
said suspected anomalous shadow detection process comprises an iris filtering process for detecting tumors, and/or a morphology filtering process for detecting microcalcifications.

7. A system for detecting suspected anomalous shadows, comprising
image obtaining means for obtaining a radiation image of a target subject,
radiation-image data obtaining means for obtaining radiation data representing the radiation image obtained by said image obtaining means of the target subject,
an anomalous shadow detecting means for detecting, based on the radiation-image data obtained by the radiation image data obtaining means, suspected anomalous shadows contained within the radiation image by performing an anomalous shadow detection process utilizing a predetermined detection parameter, further comprising
a parameter setting means for automatically setting, based on the radiation-image data of a standard phantom or an image without specifying a target subject that has been obtained by the radiation-image data obtaining means from a radiation image obtained thereof by the image obtaining means, the value of the detection parameter.

8. A system for detecting suspected anomalous shadows as defined in claim 7, wherein
the parameter setting means computes a granularity correction value, based on the granularity of the radiation-image data of the predetermined target subject, and sets the value for the detection parameter based on said granularity correction value.

9. A system for detecting suspected anomalous shadows as defined in claim 7 or 8, wherein
the parameter setting means computes a contrast correction value, based on the granularity of the radiation-image data of the predetermined target subject, and sets the value for the detection parameter based on said contrast correction value.

10. A system for detecting suspected anomalous shadows as defined in claim 7 or 8, wherein
the predetermined target subject is a standard phantom having a pattern of anomalous shadows formed of a plurality of evaluative models each of which corresponds to a different detection capability level.

11. A system for detecting suspected anomalous shadows as defined in claim 9, wherein
the predetermined target subject is a standard phantom having a pattern of anomalous shadows formed of a plurality of evaluative models each of which corresponds to a different detection capability level.

12. A method of detecting suspected anomalous shadows as defined in claim 1, wherein the standard phantom comprises a test object simulating tissue.

13. A method of detecting suspected anomalous shadows as defined in claim 1, wherein the standard phantom comprises a test object simulating radiographic characteristics of compressed tissue.

14. A method of detecting suspected anomalous shadows as defined in claim 1, wherein the standard phantom includes one of:
i) at least one of a plurality of fibers, a plurality of specks, and a plurality of masses and
ii) a surface texture pattern having a plurality of contrast gradations.

15. A system for detecting suspected anomalous shadow as defined in claim 3, wherein the standard phantom comprises a test object simulating tissue.

16. A system of detecting suspected anomalous shadows as defined in claim 3, wherein the target subject is a standard phantom comprising a test object simulating tissue.

17. A system of detecting suspected anomalous shadows as defined in claim 3, wherein the plurality of evaluative models comprise a plurality of regular geometric figures.

18. A system of detecting suspected anomalous shadows as defined in claim 17, wherein the regular geometric figures are arranged in a regular pattern.

* * * * *